(12) United States Patent
Van Dalen

(10) Patent No.: US 7,780,976 B2
(45) Date of Patent: Aug. 24, 2010

(54) APPARATUS AND METHOD FOR DELIVERING CONTROLLED QUANTITIES OF ONE OR MORE AGENTS TO THE EYE

(75) Inventor: Johan T. W. Van Dalen, Tucson, AZ (US)

(73) Assignee: Eye Care and Cure, Asia, Singapore (SG)

( * ) Notice: Subject to any disclaimer, the term of this patent is extended or adjusted under 35 U.S.C. 154(b) by 1239 days.

(21) Appl. No.: 11/347,524

(22) Filed: Feb. 3, 2006

(65) Prior Publication Data

US 2006/0127446 A1 Jun. 15, 2006

(51) Int. Cl.
*A61F 2/14* (2006.01)
*A61K 31/74* (2006.01)

(52) U.S. Cl. .................................. 424/427; 424/78.04
(58) Field of Classification Search ....................... None
See application file for complete search history.

(56) References Cited

U.S. PATENT DOCUMENTS 4,540,408 A * 9/1985 Lloyd .......................... 604/294
5,170,799 A * 12/1992 Nagase et al. ................ 600/558

* cited by examiner

*Primary Examiner*—Carlos A Azpuru
(74) *Attorney, Agent, or Firm*—Etherton Law Group, LLC; Sandra L. Etherton; Benjamin D. Tietgen

(57) ABSTRACT

A flat strip of supporting material, such as filter paper, having marked reference locations on each of one or more legs, for delivering controlled quantities of one or more agents to the adnexa of the eye simultaneously upon dispensing a liquid to the strip at the appropriate reference location.

9 Claims, 5 Drawing Sheets

APPARATUS AND METHOD FOR DELIVERING CONTROLLED QUANTITIES OF ONE OR MORE AGENTS TO THE EYE

CROSS-REFERENCE TO RELATED APPLICATIONS

This application claims the benefit of U.S. application Ser. No. 10/158,471 filed May 30, 2002, now U.S. Pat. No. 7,018,646.

FIELD OF INVENTION

This invention relates to an apparatus and method for applying controlled quantities of curative, diagnostic or therapeutic agents to the eye. This invention relates particularly to a flexible strip of supporting material incorporating one or more agents, which is wetted and touched to the surface structures of the eye.

BACKGROUND

Diagnostic, curative or therapeutic agents are administered to the eye in small quantities during ophthalmic examinations and treatments. It is often convenient to administer more than one agent at a time, such as a dye and an anesthetic, so that the eye is prepared simultaneously for multiple tests. Eye droppers and solid applicators are commonly used to administer these agents, but each has its own disadvantages.

Eye droppers are squeeze bottles that exude one drop of solution at a time, and provide multiple doses of a given agent in a single bottle. Although they are convenient, the pharmacological solutions used in the eyedroppers have disadvantages. The solutions are unstable over time and therefore have a limited shelf life. Temperature fluctuations can cause precipitation of various compounds, so less ophthalmic agent is administered to a patient than would be expected in a full solution, or an irritating solid aggregate may be dispensed into a patient's eye. Precipitation can also occur if an eye dropper bottle is not closed tightly thereby causing evaporative loss of water. After the bottles of solution are opened, the solutions may be contaminated by microbes. Over time, this microbial contamination grows and degrades the agents in solution, reducing their benefit for patients and adding the risk of infection. To deal with this problem and to increase the shelf life to a commercially-viable period of time, various preservatives are added to ophthalmic solutions to prevent microbial growth. Unfortunately, many patients are allergic to these preservatives, and the preservatives are therefore irritating to the patient's eye. Single-use vials of solution are available preservative-free, but these vials are inconvenient to use and expensive. It is desirable to provide a cost-effective, convenient dispenser of controlled quantities of ophthalmic agents that remains sterile until use, and has no preservatives.

Eyedroppers have other disadvantages. The volume of fluid dispensed by an eyedropper is often more than an eye can hold, and therefore the excess fluid leaks out. When it does, it is impossible to determine the amount of medicament administered to the eye. In addition, the liquid that leaks out of the eye can stain a patient's clothing, such as the case when fluorescein sodium, a dye commonly used in ophthalmic diagnoses, is used. Also, an eye dropper is not satisfactory when very small quantities of medications are needed, for example the quantities less than that present in one drop of a standard ophthalmic eyedropper formulation. It is desirable to administer ophthalmic agents in a way that delivers a known small quantity that remains in the patient's eye.

The prior art is replete with single-use applicators made of filter paper, plastic rods, polymer film or other dry substrate materials that are physically touched to the eye or adnexa. A solution of the agent of choice, such as fluourescein sodium, is applied to the substrate and allowed to dry. The dry, impregnated applicators are applied directly to the patient's eye, and the pharmacological agent dissolves in the patient's tears. These devices suffer serious disadvantages. First, application of a dry surface to the eye is very irritating. Second, dissolution into the tears of the eye is slow because of the extremely small volume of fluid present initially. The problem is exacerbated if the patient is suffering from dry eye syndrome, a common presenting complaint in ophthalmology. Plus, waiting for dissolution of the ophthalmic agent is a lengthy process, prolonging the irritation and discomfort for the patient. It is desirable to provide a method that delivers the agents quickly and with an applicator that is minimally irritating to the eye.

It is common practice to administer diagnostic dyes with small strips of filter paper that have been soaked in the dye and dried. To simultaneously deliver more than one agent at a time, a practitioner may add a drop of anesthetic to one end of the strip, dissolving the dye, and then touch the adnexa of the eye with the wetted filter paper. This, too, however, has its disadvantages. The filter paper is insufficiently rigid to hold the drop, and the excess fluid drops off the end of the strip. As a result, less anesthetic is given to the patient than what is in one drop, but the actual quantity is unknown, and additional anesthetic often must be administered by eyedroppers. Furthermore, upon wetting, many of the strips droop, complicating their handling. Often the dye strips are manufactured with much more dye than what is really needed for the diagnostic procedure, leading to waste, extra expense and possible damage to the patient's clothing. Practitioners in such cases wipe off the excess dye, which further illustrates the sub-optimal state of the art. Again, it is desirable to administer ophthalmic agents in a way that delivers a known quantity that remains in the patient's eye.

Additional problems arise when delivering multiple agents to the eye simultaneously. For example, it is common practice to administer a dye and an anesthetic combination during the procedure of measuring intraocular pressure using applanation or other forms of tonometry. When combined in a solution for application by eyedropper, however, many dyes and anesthetics, such as fluorescein sodium and proparacaine, form precipitates and fall out of solution or otherwise adversely affect the solubility of the companion agents. Interestingly, the same is true for the preparation of ophthalmic strips: many common ophthalmic agents form precipitates as they dry on the strip or otherwise adversely affect the solubility of the other agents, thereby rendering them useless. This means that heretofore eyedroppers and strip applicators have not been optimal delivery devices for delivering multiple agents to the eye.

Therefore, it is an object of this invention to provide an apparatus that simultaneously delivers a known quantity of one or more ophthalmic agents to the eye in a single application, with little or no waste. It is another object of this invention to provide an apparatus that delivers multiple ophthalmic agents in a disposable, sterile, single-use applicator for immediate use. It is a further object to provide an applicator having extended shelf-life with no preservatives. It is a further object of this invention to deliver ophthalmic agents in a minimally irritating way.

SUMMARY OF THE INVENTION

The present invention is a strip of supporting material for simultaneously delivering controlled quantities of one or more ophthalmic agents to the eye. The strip has one or more legs into which controlled amounts of agents are incorporated. Typically only one agent is incorporated per leg, however more than one agent may be incorporated per leg if the agents are compatible with one another and do not adversely affect the solubility of the others when combined on the strip. Each leg is marked with a reference location to show where a drop of liquid should be placed to deliver a controlled amount of agent to the eye. The reference mark is a thin line or dot of ink that does not spread or dissolve when wetted, or a notch. To use the strip, a drop of liquid, generally sterile saline or contact lens solution, is applied to one or more legs at the reference mark. The moistened strip is then applied briefly to the underside of the upper or lower eyelid, which causes transfer of the agents to the surface structures of the eye.

DETAILED DESCRIPTION OF THE INVENTION

Figure 8:
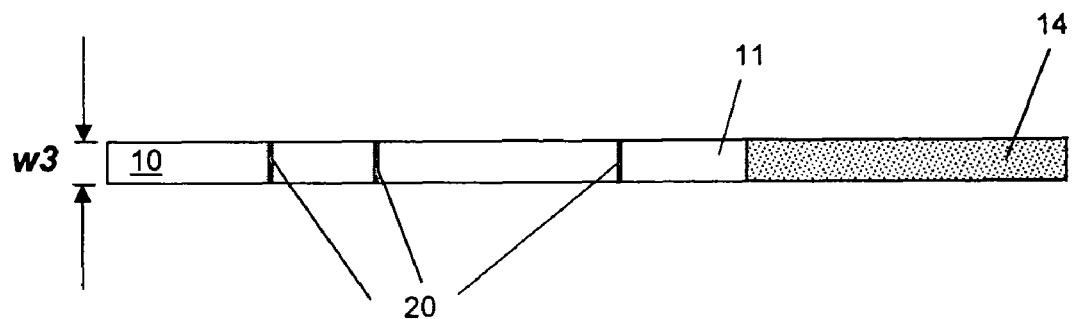
FIG. 8 is a top view of a sandwich strip with lines as reference marks.
Figure 9:
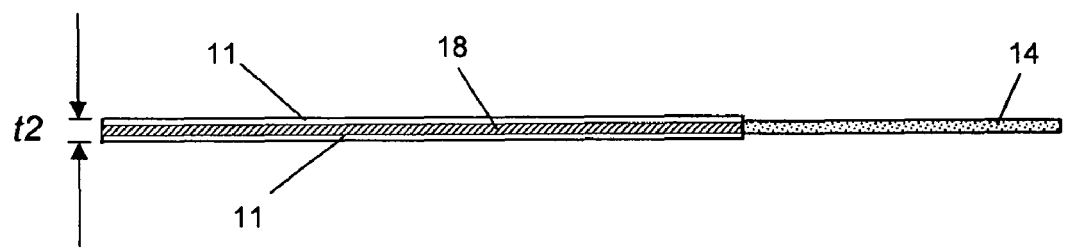
FIG. 9 is a cross-section view of the device in FIG. 8.

FIGS. 1 to 10 illustrate several embodiments of the present invention. In all embodiments, the supporting material is a strip of material that is flexible yet rigid enough to support a drop of liquid. Preferably each strip, referenced throughout generally as 10, is made of filter paper, typically methylcellulose, but may also be made of other types of paper, fabric, membrane, polymer, or other material that is physically strong enough to support the liquid and chemically compatible with the eye and ophthalmic agents. The supporting material is preferably substantially non-water soluble, but may be water soluble, substantially water soluble, or non-water soluble, depending on, among other factors, the agents used and method of manufacture. To increase convenience and decrease cost, both ends of the strip may have one or more legs 11 with incorporated agents. An alternative embodiment shown in FIGS. 8 and 9 provides a device with two legs 11 of supporting material 10 separated by a barrier 18 substantially impermeable to the liquid and ophthalmic agents, referred to herein as a sandwich device. The barrier may be positioned between the legs to form an integrated component, where one leg is attached to one side of the barrier and the other leg is attached to the other side of the barrier. Alternatively, the barrier coating may be attached to each leg on its underside, and the legs attached to the handle, with the barrier side of each leg facing one another.

Figure 1:
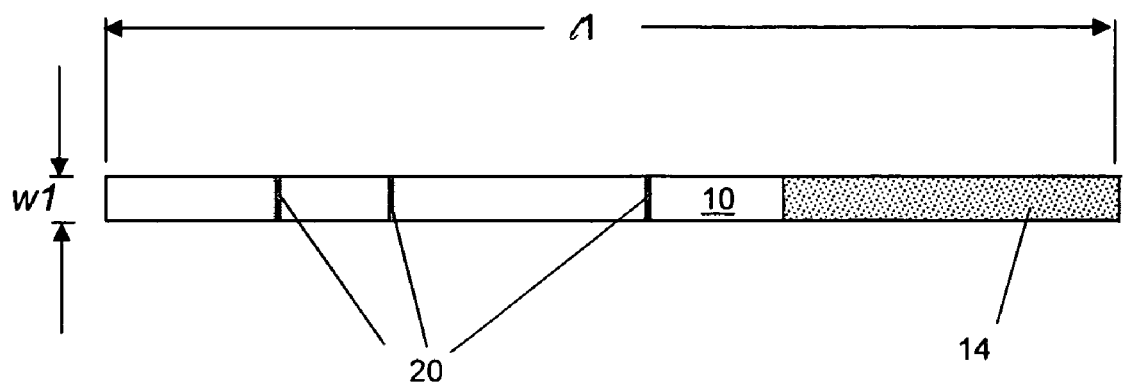
FIG. 1 is a top-view schematic illustration of a one-legged strip showing multiple reference marks.
Figure 2:
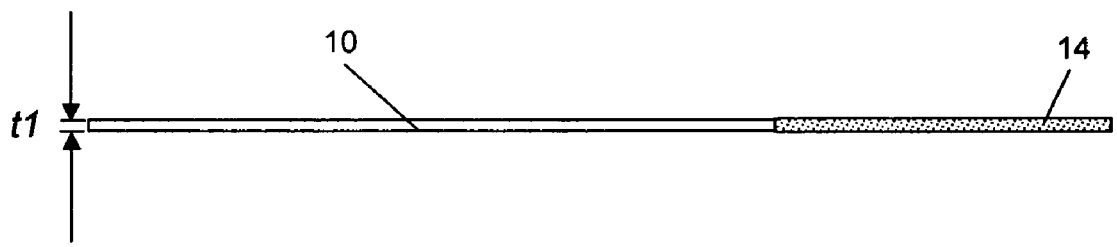
FIG. 2 is a cross-section view of the device in FIG. 1.
Figure 3:
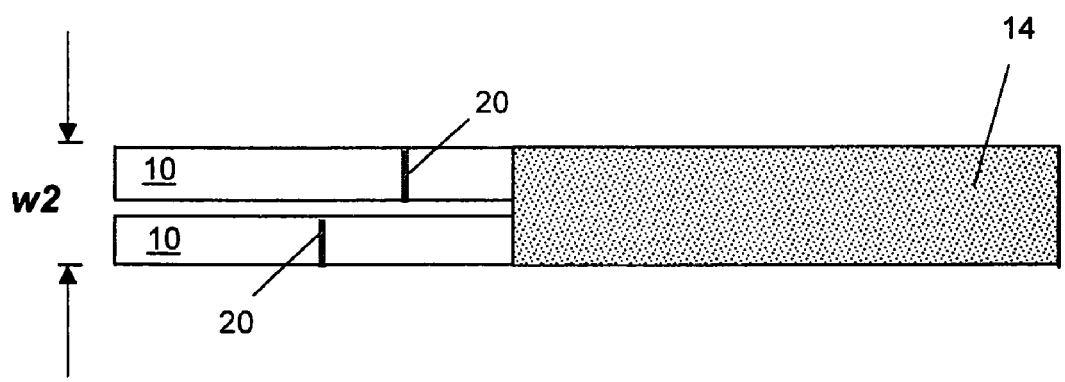
FIG. 3 is a top-view schematic illustration of a two-legged strip with lines as reference marks.
Figure 5:
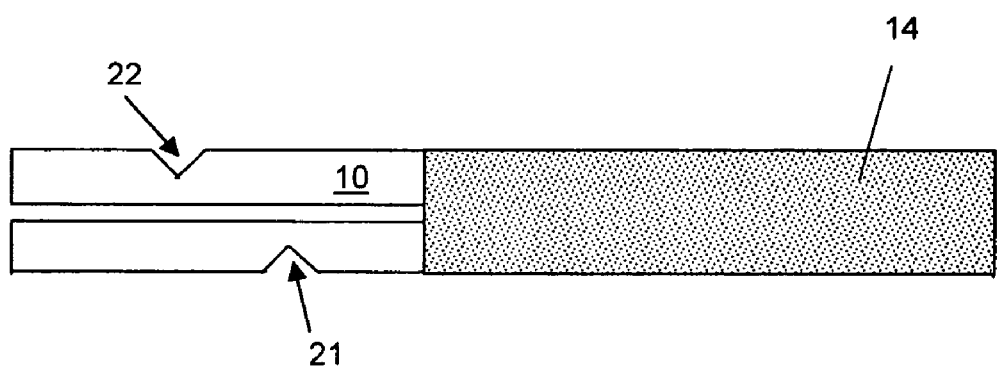
FIG. 5 is a top-view schematic illustration of a two-legged strip with notches as reference marks.
Figure 6:
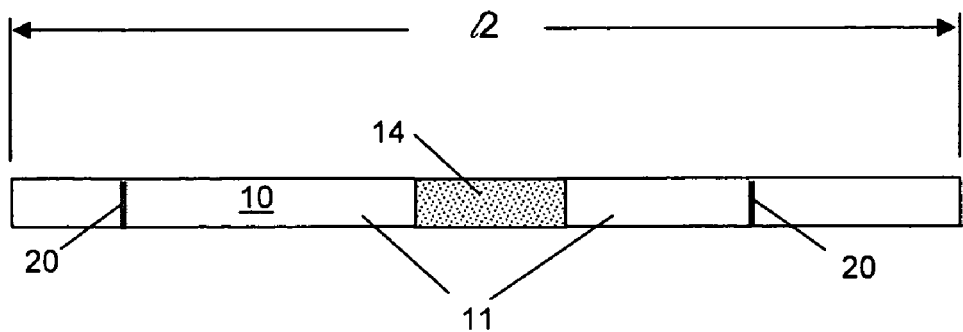
FIG. 6 is a top-view schematic illustration of a double-ended, two-legged strip with lines as reference marks.
Figure 7:
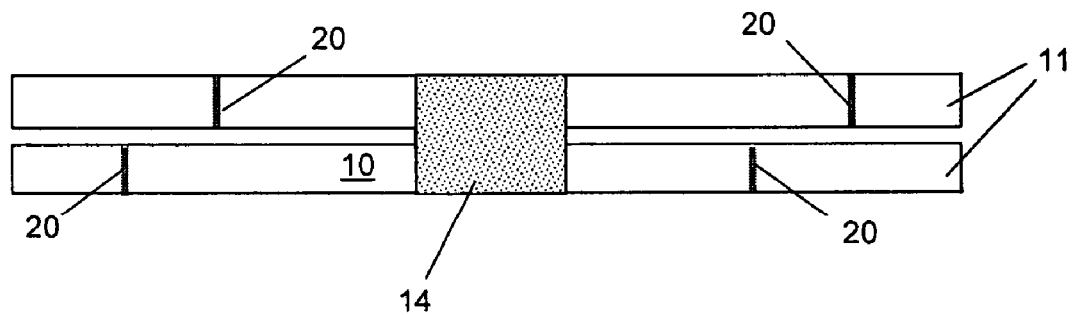
FIG. 7 is a top-view schematic illustration of a double-ended, four-legged strip with lines as reference marks.
Figure 10:
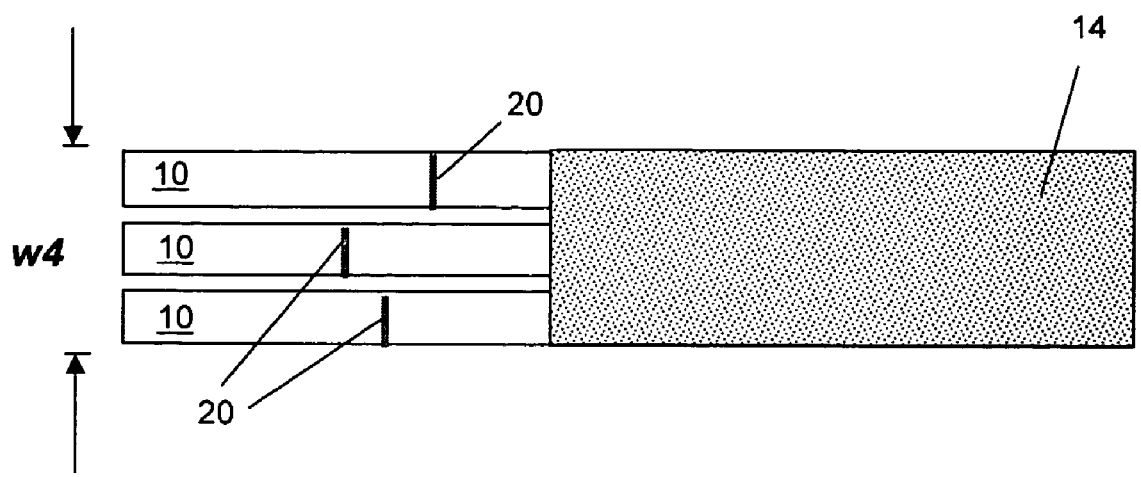
FIG. 10 is a top-view schematic illustration of a three-legged strip showing multiple reference marks.

The device is generally up to 1.5 cm in total width, indicated in FIG. 1 as w1, FIG. 3 as w2, FIG. 8 as w3 and FIG. 10 as w4. For illustration clarity, total width is indicated only on FIGS. 1, 3, 8 and 10. The device may have more than one leg 11, and the total width of the strip depends, in part, on the number of legs. Preferably each leg is about 0.5 cm wide, such that the device is 0.5 cm wide for one leg, as illustrated in FIGS. 1, 6 and 8; 1.0 cm wide for two legs attached side-by-side, such as that of FIGS. 3, 4, 5 and 7; and 1.5 cm wide for three or more legs attached side-by-side on each end, such as that of FIG. 10. The device is generally about 6 cm long for single-ended use, as indicated in FIG. 1 as t1. The device is generally about 9 cm long for double-ended use, as indicated in FIG. 6 as t2, to make the device easier to handle. For illustration clarity, length is indicated only on FIGS. 1 and 6. The single-sided device is generally about 0.03 cm thick, as illustrated in FIG. 2 as t1. The sandwich device is generally about 0.07 cm thick, as illustrated in FIG. 9 as t2.

Figure 4:
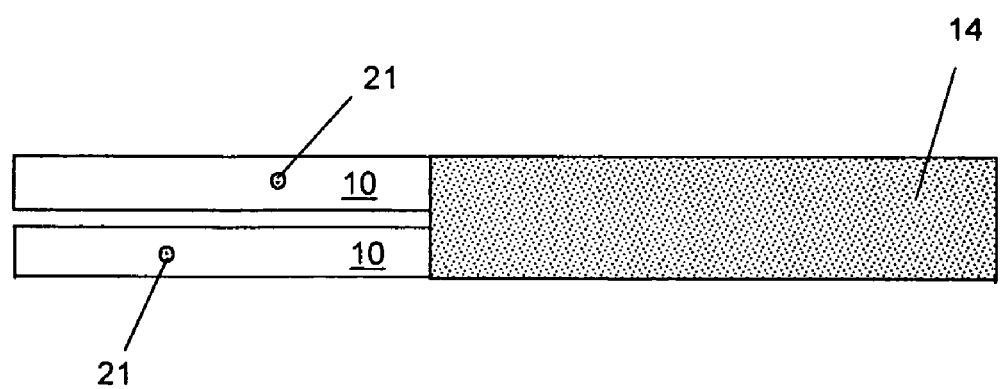
FIG. 4 is a top-view schematic illustration of a two-legged strip with dots as reference marks.

Each strip is marked with one or more visible reference marks indicating where to place a drop of liquid on each leg to deliver a controlled amount of one or more agents to the eye. The marks should be made with a substance that does not spread or dissolve when wetted. The location of the marks will depend on the desired dosage to be delivered, the concentration of the agent incorporated into the strip, and the volume of the liquid to be applied. FIG. 1 shows a graduated strip with lines 20, each marking a separate location for a drop of liquid to be applied to deliver a different dose. FIGS. 3, 6, 7, 8 and 10 show lines 20 used as reference marks for delivering single doses. Alternative types of reference marks can also be used. FIG. 4 shows dots 21 as the reference mark and FIG. 5 shows notched cut-outs 22.

A drop of liquid is applied to the filter paper at the desired location. The drop is substantially absorbed by the strip and preferably delivered by an eye dropper. The farther the liquid is placed from the end of the strip that touches the eye, the more agent is delivered to the eye. For example, if a drop of fluid is applied 0.5 centimeter from the end instead of 1.0 centimeter, half as much of the agent is delivered to the eye. For the device shown in FIGS. 8 and 9, a drop is applied to one leg, allowed to absorb, and then another drop is applied to the other leg on the other side of the strip. The liquid can be any solution that is compatible with the eye and with the agents, such as saline, distilled water, or contact solution. Preferably sterile saline is used. The liquid spreads through the paper by capillary action dissolving the incorporated compounds and bringing them toward the end of the strip. From the end of the strip, the solution of compounds is delivered by briefly touching the end of the strip to the adnexa of the eye, which rapidly draws off fluid from the end of the strip. The wetted strip is touched for a very short period, preferably no more than a second.

The strips are prepared by methods known in the art. In general, a solution having an agent of desired concentration is applied to sheets or strips of filter paper. The agent may be absorbed into or adsorbed onto the substrate, and all molecular methods of adhering the agent to the substrate are referred to herein as incorporating the agents. The substrate is preferably substantially non-water soluble, but may be water soluble, substantially water soluble, or non-water soluble, depending on, among other factors, the agents used and method of manufacture. The filter paper is dried and then cut into segments of specific size to deliver a known quantity of agent. The segments are integral with or otherwise attached to an applicator handle 14. The handle segment can be made of any suitable material that prevents moisture from being drawn from the hand holding the strip, such as varnished paper. The devices are then sealed in sterile packaging that is preferably substantially impervious to light that can deactivate the agents.

The agents can be any drug or chemical used to treat, cure, prevent, or diagnose ophthalmic problems, such as local anesthetics, diagnostic dyes, pupillary dilators, antibiotics, antivirals, antiglaucomatous preparations, nonsteroidal antiinflammatories, viral and bacterial diagnostic agents. Local anesthetics include proparacaine, and tetracaine. Diagnostic dyes include fluorescein sodium, methylene blue and rose Bengal. Typically only one agent is incorporated per leg. However, more than one agent may be incorporated per leg if the agents are compatible with one another and do not adversely affect the solubility of the others when combined on the strip.

In one example, the strips are prepared by soaking sheets or strips of filter paper first in a solution of 50 mg/ml fluorescein and then in a 45 mg/ml of proparacaine. The sheets are dried, resulting in 1.35 mg/cm$^2$ of fluorescein and 1.2 mg/cm$^2$ of proparacaine on the sheet, respectively. The sheets are then cut into segments and the reference mark is applied 1.5 cm from the applicator strip end. In another example, the strips are prepared by soaking sheets or strips of filter paper in 20 mg/ml solution of tetracaine hydrochloride, and dried, resulting in 0.540 mg/cm$^2$ tetracaine hydrochloride on the sheet. The sheets are cut into segments and the reference mark is applied 1.5 cm from the applicator strip end. The strips are then attached to a handle, packaged, and sterilized.

While there has been illustrated and described what is at present considered to be a preferred embodiment of the present invention, it will be understood by those skilled in the art that various changes and modifications may be made, and equivalents may be substituted for elements thereof without departing from the true scope of the invention. Therefore, it is intended that this invention not be limited to the particular embodiment disclosed as the best mode contemplated for carrying out the invention, but that the invention will include all embodiments falling within the scope of the appended claims.

I claim:

1. An apparatus for delivering one or more agents to the eye comprising:
    a) a strip of substantially non-water soluble supporting material for application to the eye;
    b) one or more agents incorporated into the strip; and
    c) one or more visible reference marks indicating where to place a drop of liquid on the strip to dispense a controlled amount of one or more agents to the eye.

2. The apparatus of claim 1 wherein the strip is attached to an applicator handle.

3. The apparatus of claim 1 wherein one or more agents is selected from the group of local anesthetics, diagnostic dyes, pupillary dilators, antibiotics, antivirals, antiglaucomatous preparations, nonsteroidal antiinflammatories, viral and bacterial diagnostic agents.

4. The apparatus of claim 1 wherein the agent is tetracaine hydrochloride.

5. An apparatus for delivering one or more agents to the eye comprising:
    a) a strip of substantially non-water soluble supporting material for application to the eye wherein at least one end of the strip is divided into at least two legs; and
    b) one or more agents incorporated into each of the legs such that a controlled amount of each agent is delivered to the eye upon application of liquid to each leg.

6. The apparatus of claim 5 wherein the strip is attached to an applicator handle.

7. The apparatus of claim 5 wherein one or more agents is selected from the group of local anesthetics, diagnostic dyes, pupillary dilators, antibiotics, antivirals, antiglaucomatous preparations, nonsteroidal antiinflammatories, viral and bacterial diagnostic agents.

8. The apparatus of claim 5 further wherein a first leg incorporates dye and a second leg incorporates anesthetic.

9. The apparatus of claim 5 wherein the legs are separated by a barrier substantially impermeable to the agents and the liquid.

* * * * *